US007767855B2

(12) United States Patent
Haese et al.

(10) Patent No.: US 7,767,855 B2
(45) Date of Patent: Aug. 3, 2010

(54) METHOD FOR THE CONTINUOUS PRODUCTION OF AN AMINE

(75) Inventors: Frank Haese, Bollingstedt (DE); Joachim Wulff-Doering, Frankenthal (DE); Ulrich Koehler, Mannheim (DE); Peter Gaa, Worms (DE); Frank-Friedrich Pape, Kleinniedesheim (DE); Johann-Peter Melder, Boehl-Iggelheim (DE); Manfred Julius, Limburgerhof (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 11/993,891

(22) PCT Filed: Jun. 21, 2006

(86) PCT No.: PCT/EP2006/063387

§ 371 (c)(1), (2), (4) Date: Dec. 26, 2007

(87) PCT Pub. No.: WO2006/136573

PCT Pub. Date: Dec. 28, 2006

(65) Prior Publication Data

US 2008/0200726 A1 Aug. 21, 2008

(30) Foreign Application Priority Data

Jun. 23, 2005 (DE) ....................... 10 2005 029 095

(51) Int. Cl.
*C07C 211/00* (2006.01)

(52) U.S. Cl. ...................................................... 564/305

(58) Field of Classification Search ....................... None
See application file for complete search history.

(56) References Cited

U.S. PATENT DOCUMENTS

| | | | | |
|---|---|---|---|---|
| 3,275,554 | A | 9/1966 | Wagenaar | |
| 3,751,475 | A | 8/1973 | van der Voot et al. | |
| 3,931,298 | A | 1/1976 | Wollensak | |
| 3,960,962 | A | 6/1976 | Shubkin | |
| 4,252,742 | A | 2/1981 | Blackwell, III et al. | |
| 4,429,155 | A | 1/1984 | Göetz et al. | |
| 4,832,702 | A | 5/1989 | Kummer et al. | |
| 5,072,044 | A | 12/1991 | Herkes | |
| 5,663,438 | A * | 9/1997 | Kohler et al. | 564/305 |
| 5,958,825 | A * | 9/1999 | Wulff-Doring et al. | 502/300 |
| 6,049,007 | A * | 4/2000 | Riechers et al. | 564/302 |
| 6,057,442 | A * | 5/2000 | Wulff-Doring et al. | 544/106 |
| 6,821,396 | B2 | 11/2004 | Wolfert et al. | |
| 6,913,674 | B2 | 7/2005 | Wölfert et al. | |
| 6,986,833 | B2 | 1/2006 | Wölfert et al. | |

FOREIGN PATENT DOCUMENTS

| | | |
|---|---|---|
| CN | 1207329 | 2/1999 |
| DE | 2125039 | 12/1971 |
| DE | 3611230 | 10/1987 |
| EP | 0022751 | 1/1981 |
| EP | 0053819 | 6/1982 |
| EP | 0167996 | 1/1986 |
| EP | 0701995 | 3/1996 |
| EP | 1312599 | 5/2003 |
| EP | 1312600 | 5/2003 |
| GB | 1344574 | 1/1974 |

OTHER PUBLICATIONS

Jiang et al, {Characterization and performance of Pd-La/spinel catalyst for preparation of 2,6-diisopropylaniline, Applied Catalysis, A: General (2003), 250(2), 209-220}.*

"Fixed-Bed Reactors," *Ullman's Encyclopedia of Industrial Chemistry*, 5th Ed., vol. B4, pp. 199-238.

* cited by examiner

*Primary Examiner*—Jafar Parsa
*Assistant Examiner*—Chukwuma O Nwaonicha
(74) *Attorney, Agent, or Firm*—Connolly Bove Lodge & Hutz LLP

(57) ABSTRACT

Processes comprising: providing an aromatic alcohol; and reacting the aromatic alcohol with ammonia at a temperature of 80 to 350° C. in the presence of hydrogen and a heterogeneous catalyst to form a crude reaction product comprising a corresponding primary aromatic amine, wherein the heterogeneous catalyst comprises a catalytically active composition which, prior to reduction with hydrogen, comprises 90 to 99.8% by weight of zirconium dioxide ($ZrO_2$), 0.1 to 5.0% by weight of an oxygen-comprising compound of palladium, and 0.1 to 5.0% by weight of an oxygen-comprising compound of platinum.

19 Claims, No Drawings

METHOD FOR THE CONTINUOUS PRODUCTION OF AN AMINE

The present invention relates to a process for the continuous preparation of a primary aromatic amine by reaction of a corresponding aromatic alcohol with ammonia in the presence of hydrogen at a temperature in the range from 80 to 350° C. in the presence of a heterogeneous catalyst.

The process products are used, inter alia, as intermediates in the production of fuel additives (U.S. Pat. No. 3,275,554, DE-A-21 25 039 and DE-A-36 11 230), surfactants, drugs and crop protection agents, hardeners for epoxy resins, catalysts for polyurethanes, intermediates for preparing quaternary ammonium compounds, plasticizers, corrosion inhibitors, synthetic resins, ion exchangers, textile assistants, dyes, vulcanization accelerators and/or emulsifiers.

U.S. Pat. No. 5,072,044 (Du Pont) discloses the dehydrogenation of cyclohexylamines to form the corresponding aromatic amines over Li-doped Pd catalysts. The reaction requires higher reaction temperatures of 360-380° C., which promotes the formation of undesirable by-products.

EP-A-701 995 (BASE AG) describes a process for the preparation of aromatic amines from the corresponding cycloaliphatic amines in the presence of hydrogen and ammonia over a bimetallic palladium/platinum catalyst. For this purpose, the cycloaliphatic amine firstly has to be made available by means of another process.

EP-A-22 751 (Ciba-Geigy AG) describes the reaction of phenols in the presence of ammonia and hydrogen in the presence of noble metal catalysts comprising alumina or carbon as support material to form the corresponding cyclohexylamines. This text teaches nothing about the preparation of aromatic amines.

EP-A-53 819 (BASF AG) discloses a process for the preparation of cycloaliphatic and/or aromatic amines from phenols. The catalyst system used comprises Ru, Rh or Pt on an aluminum oxide support.

EP-A-167 996 (BASF AG) describes a process for the preparation of aromatic amines by reaction of the corresponding phenol, if appropriate in the presence of the corresponding recirculated cycloaliphatic amine, in the presence of ammonia and hydrogen over a noble metal catalyst at atmospheric pressure in two reaction zones connected in series. Preference is given to catalysts supported on aluminum oxide.

CA Abstract No. 132:336078 (CN-1 087 970) relates to the synthesis of 2,6-dimethylaniline from 2,6-dimethylphenol at 180-200° C. over a specific $Pd/Al_2O_3$—$MgO/Al_2O_3$ catalyst.

It was an object of the present invention to overcome a disadvantage or a plurality of disadvantages of the prior art and discover an improved economical process for the preparation of a primary aromatic amine. In particular, the process should make better yields, space-time yields (STYs) and/or selectivities possible. The catalyst used should make improved operating lives and thus less frequent regenerations possible.

[Space-time yields are given in "amount of product/(catalyst volume●time)" (kg/($l_{cat}$●h)) and/or "amount of product/(reactor volume●time)" (kg/($l_{reactor}$●h))].

This object has been able to be achieved by carrying out the synthesis in the liquid phase or in the gas phase over a bimetallic palladium/platinum catalyst comprising a $ZrO_2$ support.

We have accordingly found a process for the continuous preparation of a primary aromatic amine by reaction of a corresponding aromatic alcohol with ammonia in the presence of hydrogen at a temperature in the range from 80 to 350° C. in the presence of a heterogeneous catalyst, wherein the catalytically active composition of the catalyst before reduction with hydrogen comprises from 90 to 99.8% by weight of zirconium dioxide ($ZrO_2$), from 0.1 to 5.0% by weight of oxygen-comprising compounds of palladium and from 0.1 to 5.0% by weight of oxygen-comprising compounds of platinum.

For the synthesis in the gas phase, the starting alcohol is vaporized in a targeted manner, preferably in a circulating gas stream , and fed in gaseous form into the reactor. The circulating gas serves firstly for vaporization of the starting alcohol and secondly as reactant for the amination.

In the gas recycle mode, the starting materials (alcohol, hydrogen and ammonia) are vaporized and fed in gaseous form in a circulating gas stream into the reactor. The starting materials (alcohol and ammonia) can also be vaporized as aqueous solutions and conveyed with the circulating gas stream into the catalyst bed.

Preferred reactors are tube reactors. Examples of suitable reactors with a circulating gas stream may be found in Ullmann's Encyclopedia of Industrial Chemistry, 5th Ed., Vol. B 4, pages 199-238, "Fixeded Reactors".

As an alternative, the reaction is advantageously carried out in a shell-and-tube reactor or in a single-stream plant.

In the case of a single-stream plant, the tube reactor in which the reaction occurs can comprise a plurality (e.g. two or three) of individual tube reactors connected in series. Optionally, it may be advantageous here to introduce feed (comprising the starting S material and/or ammonia and/or $H_2$) and/or circulating gas and/or reactor output from a downstream reactor at an intermediate point.

The amount of circulating gas is preferably in the range from 40 to 1500 $m^3$ (at operating pressure)/[$m^3$ of catalyst (bed volume)·h], in particular in the range from 100 to 700 $m^3$ (at operating pressure)/[$m^3$ of catalyst (bed volume)·h].

The circulating gas preferably comprises at least 10% by volume, particularly preferably from 50 to 100% by volume, very particularly preferably from 80 to 100% by volume, of $H_2$.

For the synthesis in the liquid phase, all starting materials and products which do not readily vaporize or are thermally labile are suitable. In these cases, a further advantage is that vaporization and recondensation of the amine in the process can be dispensed with.

In the process of the invention, the catalysts are preferably used in the form of catalysts which consist entirely of catalytically active composition and, if appropriate, a shaping aid (e.g. graphite or stearic acid) if the catalyst is used as shaped body, i.e. comprise no further catalytically active accompanying substances. In this context, the oxidic support material zirconium dioxide (ZrO2) is regarded as part of the catalytically active composition.

To use the catalysts, it is possible either to introduce the catalytically active composition which has been milled to powder into the reaction vessel or to install the catalytically active composition in the reactor as shaped catalyst bodies, for example as pellets, spheres, rings, extrudates (e.g., rods), after milling, mixing with shaping aids, shaping and heat treatment.

The concentrations (in % by weight) reported for the components of the catalyst are in each case based, unless indicated otherwise, on the catalytically active composition of the finished catalyst after its last heat treatment and before reduction with hydrogen.

The catalytically active composition of the catalyst after its last heat treatment and before reduction with hydrogen is defined as the sum of the catalytically active constituents and the abovementioned catalyst support materials and comprises essentially the following constituents: zirconium dioxide ($ZrO_2$), oxygen-comprising compounds of palladium and oxygen-comprising compounds of platinum.

The sum of the abovementioned constituents of the catalytically active composition is usually from 70 to 100% by weight, preferably from 80 to 100% by weight, particularly preferably from 90 to 100% by weight, especially >95% by weight, very especially >98% by weight, in particular >99% by weight, e.g. particularly preferably 100% by weight.

The catalytically active composition of the catalysts used in the process of the invention can further comprise one or more elements (oxidation state 0) or their inorganic or organic compounds selected from among groups I A to VI A and I B to VII B and VIII of the Periodic Table.

Examples of such elements and compounds thereof are: transition metals such as Co to CoO, Re or rhenium oxides, Mn or $MnO_2$, Mo or molybdenum oxides, W or tungsten oxides, Ta or tantalum oxides, Nb or niobium oxides or niobium oxalate, V or vanadium oxides or vanadyl pyrophosphate; lanthanides such as Ce or $CeO_2$ or Pr or $Pr_2O_3$; alkalimetal oxides such as $Na_2O$; alkalimetal carbonates; alkaline earth metal oxides such as SrO; alkaline earth metal carbonates such as $MgCO_3$, $CaCO_3$ and $BaCO_3$; boron oxide ($B_2O_3$).

The catalytically active composition of the catalysts used in the process of the invention preferably comprises no ruthenium, no copper, no cobalt, no iron and/or no nickel. The catalytically active composition of the catalysts used in the process of the invention comprises, after its last heat treatment and before reduction with hydrogen, from 90 to 99.8% by weight, preferably from 98 to 99.6% by weight, particularly preferably from 98.8 to 99.2% by weight, of zirconium dioxide ($ZrO_2$), from 0.1 to 5.0% by weight, preferably from 0.2 to 1.0% by weight, particularly preferably from 0.4 to 0.6% by weight, of oxygen-comprising compounds of palladium and from 0.1 to 5.0% by weight, preferably from 0.2 to 1.0% by weight, particularly preferably from 0.4 to 0.6% by weight, of oxygen-comprising compounds of platinum.

Various methods of producing the catalysts used in the process of the invention are possible. Mention may here be made of, for example, the known precipitation methods.

The catalysts used in the process of the invention can be produced by, in particular, impregnation of zirconium dioxide ($ZrO_2$) which may be present, for example, in the form of powder or shaped bodies such as extrudates, pellets, spheres or rings.

The zirconium dioxide is used, for example, in the monoclinic or tetragonal form, preferably in the monoclinic form.

Shaped bodies can be produced by customary methods.

Impregnation is likewise carried out by customary methods, e.g. as described in A. B. Stiles, Catalyst Manufacture—Laboratory and Commercial Preparations, Marcel Dekker, New York (1983), by application of an appropriate metal salt solution in one or more impregnation stages, using, for example, appropriate nitrates, acetates or chlorides as metal salts. After impregnation, the composition is dried and optionally calcined.

Impregnation can be carried out by the "incipient wetness" method, in which the zirconium dioxide is moistened with an amount of impregnation solution which is no more than that corresponding to its water uptake capacity. However, impregnation can also be carried out in an excess of solution.

In the case of multistage impregnation methods, it is advantageous to dry and optionally calcine the composition between individual impregnation steps. Multistage impregnation is particularly advantageous when a relatively large amount of metal is to be applied to the zirconium dioxide.

To apply the metal components to the zirconium dioxide, impregnation can be carried out simultaneously with all metal salts or with the individual metal salts in succession in any order.

After calcination, which is, for example, carried out at a temperature in the range from 200 to 600° C., the catalyst is advantageously conditioned, either by bringing it to a particular particle size by milling or by mixing it after milling with shaping aids such as graphite or stearic acid, pressing the mixture by means of a press to give shaped bodies, e.g. pellets, and heat-treating these. The heat treatment temperatures preferably correspond to the temperatures in the calcination.

The catalysts produced in this way comprise the catalytically active metals in the form of a mixture of their oxygen-comprising compounds, i.e. in particular as oxides and mixed oxides.

The catalysts produced in this way are stored and, if appropriate, sold in this form. Before use as catalysts, they are usually prereduced. However, they can also be used without prereduction, in which case they are then reduced by the hydrogen present in the reactor under the conditions of the hydrogenative amination.

For the purposes of prereduction, the catalysts are firstly exposed to a nitrogen/hydrogen atmosphere at preferably from 150 to 200° C. for a period of, for example, from 12 to 20 hours and are subsequently treated in a hydrogen atmosphere at preferably from 200 to 400° C. for up to about 24 hours. In this prereduction, part of the oxygen-comprising metal compounds present in the catalysts is reduced to the corresponding metals, so that the latter are present together with the various oxygen compounds in the active form of the catalyst.

The $Pd/Pt/ZrO_2$ catalysts disclosed in EP-A-701 995 (BASF AG) are particularly preferably used in the process of the invention.

The process of the invention is carried out continuously, with the catalyst preferably being arranged as a fixed bed in the reactor. Flow through the fixed bed of catalyst can be either from the top or from the bottom. The temperature, pressure and amount of the gas stream are set so that even relatively high-boiling reaction products remain in the gas phase.

The aminating agent ammonia can be used in stoichiometric, substoichiometric or superstoichiometric amounts relative to the alcoholic hydroxyl group to be aminated.

Ammonia is generally used in a from 1.5- to 250-fold, preferably from 2- to 100-fold, in particular from 2- to 10-fold, molar excess per mole of alcoholic hydroxyl group to be reacted.

Higher excesses of ammonia are possible.

The process is preferably operated with an amount of off-gas of from 5 to 800 standard cubic meters/h, in particular from 20 to 300 standard cubic meters/h.

When working in the liquid phase, the starting materials (alcohol plus ammonia) are simultaneously passed in the liquid phase at pressures of generally from 5 to 30 MPa (50-300 bar), preferably from 5 to 25 MPa, particularly preferably from 15 to 25 MPa, and temperatures of generally from 80 to 350° C., especially from 100 to 300° C., preferably from 120 to 270° C., particularly preferably from 130 to 250° C., in particular from 170 to 230° C., including hydrogen, over the catalyst which is usually located in a fixed-bed reactor which is preferably heated from the outside. Operation in both the downflow mode and in the upflow mode is possible. The space velocity over the catalyst is generally in the range from 0.05 to 5 kg, preferably from 0.1 to 2 kg, particularly preferably from 0.2 to 0.6 kg, of alcohol per liter of catalyst (bed volume) and hour. The starting materials can, if appropriate, be diluted with a suitable solvent such as tetrahydrofuran, dioxane, N-methyl-pyrrolidone or ethylene glycol dimethyl ether. It is advantageous to heat the reactants before they are fed into the reaction vessel, preferably to the reaction temperature.

When working in the gas phase, the gaseous starting materials (alcohol plus ammonia) are vaporized in a gas stream which is sufficiently large for vaporization, preferably hydrogen, and passed at pressures of generally from 0.1 ° C. to 40 MPa (1-400 bar), preferably from 0.1 to 10 MPa, particularly preferably from 0.1 ° C. to 5 MPa, in the presence of hydrogen over the catalyst. The temperatures for the amination are generally from 80 to 350° C., especially from 100 to 300° C., preferably from 120 to 290° C., particularly preferably from 160 to 280° C. The flow into the fixed bed of catalyst can be either from above or from below. The gas stream required is preferably obtained by means of a gas recycle mode of operation.

The space velocity of the catalyst is generally in the range from 0.01 to 2 kg, preferably from 0.05 to 0.5 kg, of alcohol per liter of catalyst (bed volume) and hour.

The hydrogen is generally fed into the reaction in an amount of from 5 to 400 l, preferably in an amount of from 50 to 200 l, per mole of alcohol component, with the liter figures being based in each case on S.T.P.

Both when working in the liquid phase and when working in the gas phase, higher temperatures and higher total pressures and space velocities over the catalyst are possible. The pressure in the reaction vessel, which is the sum of the partial pressures of the aminating agent, the alcohol and the reaction products formed and also any solvent used at the temperatures indicated, is advantageously increased to the desired reaction pressure by injection of hydrogen.

Both in continuous operation in the liquid phase and in continuous operation in the gas phase, the excess aminating agent can be circulated together with the hydrogen.

If the catalyst is arranged as a fixed bed, it can be advantageous in terms of the selectivity of the reaction to mix the shaped catalyst bodies with inert packing elements in the reactor, i.e. to "dilute" them. The proportion of packing elements in such catalyst preparations can be from 20 to 80 parts by volume, preferably from 30 to 60 parts by volume and in particular from 40 to 50 parts by volume.

The water of reaction formed during the reaction (in each case one mole per mole of alcohol group reacted) generally does not have any adverse effect on the conversion, the reaction rate, the selectivity and the operating life of the catalyst and is therefore advantageously removed from the reaction product only in the work-up of the reaction product, e.g. by distillation.

The reaction product mixture is advantageously depressurized and the excess hydrogen and any excess aminating agent present are then removed and the crude reaction product obtained is purified, e.g. by means of fractional rectification. The excess aminating agent and the hydrogen are advantageously recirculated to the reaction zone. The same applies to any incompletely reacted alcohol component.

The respective pure products can be obtained from the crude products by rectification using known methods. The pure products are obtained as azeotropes with water or can be dewatered by means of liquid-liquid extraction with concentrated sodium hydroxide solution using methods based on those described in the patent applications EP-A-1 312 599 and EP-A-1 312 600. This dewatering can be carried out before or after the purification by distillation. Dewatering by distillation in the presence of an entrainer using known methods is also possible.

If the crude product or the aromatic amine in the crude product is sparingly miscible or immiscible with water, dewatering by means of separation of the organic phase and the aqueous phase using known methods is also possible. According to the procedure taught in EP-A-1 312 599 and EP-A-1 312 600 (both BASF AG), one or more low-boiling fractions can be separated off from the separated amine-comprising organic phase by distillation. In a further step, it is possible to separate off one or more low-boiling fractions from the amine-comprising mixture by distillation. In a subsequent distillation step, the essentially water-free amine can be obtained in pure form from the mixture as bottom offtake stream or side offtake stream from the column, and this may, if appropriate, be subjected to further purification or fractionation.

The individual steps for purifying the amine can, if appropriate, also be carried out batchwise or continuously in a single column, with the low boilers being able to be separated off via the top offtake and/or the side offtake of the rectification section of the column, the high-boiling fractions being able to be separated off via the bottom offtake of the distillation column and the pure amine being able to be separated off via the side offtake in the stripping section of the column.

In a particularly preferred variant, a dividing wall column is used as continuous distillation column.

Unreacted starting materials and any suitable by-products obtained can be recirculated to the synthesis. After condensation of the products in a separator, unreacted starting materials can once again be passed, in discontinuous or continuous operation, in the circulating gas stream over the catalyst bed.

The use of ammonia as aminating agent results in conversion of the alcoholic hydroxyl group of the aromatic alcohol used into a primary amino group ($—NH_2$) with retention of the position on the aromatic ring.

Suitable aromatic alcohols include virtually all alcohols having an aromatic OH function, i.e. the OH group is bound to an $sp^2$-hybridized carbon atom in an aromatic ring. Apart from the carbon atoms, the aromatic ring can also have one or more heteroatoms such as N, O or S. The alcohols can also bear substituents or comprise functional groups which are inert under the conditions of the hydrogenative amination, for example alkoxy, alkenyloxy, alkylamino or dialkylamino groups, or may be hydrogenated under the conditions of the hydrogenative amination, for example C—C double or triple bonds. If polyhydric aromatic alcohols are to be aminated, corresponding amino alcohols or multiply aminated products can be obtained by means of control of the reaction conditions.

Preference is given to aminating, for example, the following aromatic alcohols: phenol, where the phenyl radical may bear one or more alkyl radicals, in particular $C_{1-9}$-alkyl radicals and $C_{5-6}$-cycloalkyl radicals, and/or aryl radicals as substituents, 1- or 2-naphthol, where the naphthyl radical may bear one or more alkyl radicals, in particular $C_{1-9}$-alkyl radicals and $C_{5-6}$-cycloalkyl radicals, and/or aryl radicals as substituents.

$C_{1-9}$-Alkyl radicals, preferably $C_{1-3}$-alkyl radicals, are, for example, methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, cyclopentylmethyl, n-heptyl, isoheptyl, cyclohexylmethyl, n-octyl, isooctyl, 2-ethylhexyl, n-nonyl.

Aryl radicals are, for example, phenyl, 1-naphthyl, 2-naphthyl.

Examples are: ortho-, meta- and para-cresol, ortho-ethylphenol, ortho-n-butyl phenol, owtho-sec-butylphenol, 2,4-dimethyl phenol, 2,6-dimethylphenol, 2,3,6-trimethylphenol, 2,4,6-trimethylphenol, 2-cyclohexylphenol, 2,6-dimethyl-3-cyclohexylphenol, 2,6-diethylphenol, 2,5-diisopropylphenol, 2-methyl-6-sec-butylphenol, 3-tert-butylphenol, 2,6-diisopropyiphenol, 2,6-di-sec-butylphenol, 2,6-dicyclohexylphenol, alpha-naphthol, beta-naphthol, bisphenol A (=2,2-di(p-hydroxyphenyl)propane, hydroquinone, monoalkylhydroquinones, dialkylhydroquinones, trialkylhydroquinone or tetraalkylhydroquinones, in particular hydroquinones substituted by (independently of one another) $C_{1-9}$-alkyl radicals, e.g. monomethylhydroquinone, tetramethylhydroquinone.

The aromatic alcohols used as starting material, in particular phenols, are readily available compounds (e.g. Houben Weyl, Methoden, Volume 6/lc).

Aromatic amines which are preferably prepared by the process of the invention are 2,6-di($C_{1-9}$-alkyl)anilines from the corresponding 2,6-di($C_{1-9}$-alkyl)phenols. Examples are 2,6-dimethylaniline (2,6-xylidine), 2,6-diethylaniline, 2-methyl-6-ethylaniline, 2,6-diisopropylaniline, 2-isopropyl-6-methylaniline and 2-isopropyl-6-ethylaniline.

An aromatic amine which is particularly preferably prepared by the process of the invention is 2,6-dimethylaniline (2,6-xylidine), which is obtained by reaction of 2,6-dimethylphenol.

The process of the invention, in particular the process according to claim 17 or 18, makes it possible to prepare, in particular, 2,6-dimethylaniline (2,6-xylidine) having a purity of ≧99% by weight, particularly preferably ≧99.5% by weight, very particularly preferably ≧99.85% by weight, and a 2,6-dimethylphenol content of ≦0.1% by weight, particularly preferably ≦0.05% by weight, very particularly preferably ≦0.02% by weight, e.g. from 0 to 0.015% by weight, from 2,6-dimethylphenol and ammonia.

The abovementioned contents in % by weight were determined as follows by gas chromatography:

| | |
|---|---|
| Separation column: | DB WAX (polyethylene glycol) |
| Length (m): | 30 |
| Film thickness (μm): | 0.5 |
| internal diameter (mm): | 0.25 |
| Carrier gas: | Helium |
| Inlet pressure (bar): | 1.0 |
| Split (ml/min): | 100 |
| Septum flushing (ml/min): | 4 |
| Oven temperature (° C.): | 80 |
| Preheating time (min): | 3 |
| Rate (° C./min): | 5 |
| Oven temperature (° C.): | 240 |
| After-heating time (min): | 30 |
| Injector temperature (° C.): | 250 |
| Detector temperature (° C.): | 260 |
| Injection: | HP 7673 Autosampler |
| Injection volume (μl): | 0.2 |
| Detector type: | FID |
| GC method: | GC-% by area method |

Description of Sample Preparation:

The sample is, if appropriate, melted at 60° C. for 4 hours (2,6-dimethylphenol melts at about 45° C.). About 1 g of the molten sample is dissolved in 50 ml of dichloromethane and analyzed.

The 2,6-dimethylphenol used in the process of the invention to prepare 2,6-dimethylaniline preferably has the following specification:

| | |
|---|---|
| Assay | min. 99.5% by weight |
| Cresols (all isomers) | max. 1500 ppm |
| Xylenols (all isomers) | max. 1000 ppm |
| Anisole | max. 1000 ppm |
| Phenol | max. 100 ppm |
| Moisture | max. 0.5% by weight |
| Sulfur | max. 1 ppm |
| Chlorine | max. 1 ppm |
| Bromine | max. 1 ppm |

ppm figures are by weight.

The determination of water is carried out by means of Karlischer titration.

Determination of Sulfur:

Coulometric determination via combustion
Instrument: Euroglas (LHG), model ECS 1200;
Reference: DIN 51400 part 7

Determination of Halogen:

Coulometric determination via combustion
Instrument: Euroglas (LHG), model ECS 1200
References: F. Ehrenberger "Quantitative organische Elementaranalyse"
ISBN 3-527-28056-1
DIN 51408 part 2, "Bestimmung des Chlorgehaltes"

EXAMPLES

All examples were carried out using the bimetallic palladium/platinum catalyst described in Example 4 (page 6, lines 12-15) of EP-B1-701 995 (BASF AG), and this was also activated by the method described there (page 4, lines 47-52). The supported noble metal catalyst was then installed in the reactor and subsequently reduced in a stream of nitrogen/hydrogen at 200° C. under atmospheric pressure or under the operating pressure.

Preparation of 2,6-dimethylaniline

A circulating gas stream comprising 170 kg/h of ammonia and 20 kg/h of hydrogen was established at a total pressure of 2 bar in two reactors connected in series which were each charged with 10 liters of catalyst. 122 kg/h of 2,6-dimethylphenol were introduced continuously into this stream and vaporized. The gaseous mixture was passed over the catalyst bed of the first reactor at 200-220° C. and over the catalyst bed of the second reactor at 230-270° C. The yield of 2,6-xylidine after the second reactor was 95%.

The invention claimed is:

1. A process for making a crude reaction product comprising: providing an aromatic alcohol; and reacting the aromatic alcohol with ammonia at a temperature of 80 to 350° C. in the presence of hydrogen and a heterogeneous catalyst to form the crude reaction product comprising a corresponding primary aromatic amine, wherein the heterogeneous catalyst comprises a catalytically active composition which, prior to reduction with hydrogen, comprises 90 to 99.8% by weight of zirconium dioxide ($ZrO_2$), 0.1 to 5.0% by weight of an oxygen-comprising compound of palladium, and 0.1 to 5.0% by weight of an oxygen-comprising compound of platinum; and wherein the reaction is carried out in a single-stream plant comprising a plurality of tube reactors connected in series.

2. The process according to claim 1, wherein the single-stream plant comprises two or three tube reactors connected in series.

3. The process according to claim 1, wherein the reaction is carried out at a temperature of 120 to 300° C.

4. The process according to claim 1, wherein the reaction is carried out in a liquid phase at an absolute pressure of 5 to 30 MPa.

5. The process according to claim 1, wherein the reaction is carried out in a gas phase at an absolute pressure of 0.1 to 40 MPa.

6. The process according to claim 1, wherein the catalytically active composition, prior to reduction with hydrogen, comprises 98 to 99.6% by weight of zirconium dioxide ($ZrO_2$), 0.2 to 1.0% by weight of an oxygen-comprising compound of palladium, and 0.2 to 1.0% by weight of an oxygen-comprising compound of platinum.

7. The process according to claim 1, wherein the aromatic alcohol is reacted with an amount of ammonia which is a 1.5- to 250-fold molar amount based on the aromatic alcohol.

8. The process according to claim 1, wherein the aromatic alcohol is reacted with an amount of ammonia which is a 2.0- to 10-fold molar amount based on the aromatic alcohol.

9. The process according to claim 1, wherein the heterogeneous catalyst comprises a fixed bed.

10. The process according to claim 1, wherein the reaction is carried out in a gas recycle mode.

11. The process according to claim 1, wherein the alcohol is provided as an aqueous solution.

12. The process according to claim 1, wherein the ammonia is provided as an aqueous solution.

13. The process according to claim 1, wherein the corresponding primary aromatic amine comprises a phenylamine which may optionally be substituted with one or more $C_{1-9}$-alkyl radicals.

14. The process according to claim 1, wherein the aromatic alcohol comprises phenol and the corresponding aromatic amine comprises aniline.

15. The process according to claim 1, wherein the corresponding aromatic amine comprises a 2,6-di($C_{1-9}$-alkyl) aniline.

16. The process according to claim 11, wherein the aromatic alcohol comprises 2,6-dimethylphenol and the corresponding aromatic amine comprises 2,6- dimethylaniline.

17. The process according to claim 1, further comprising separating an organic phase comprising the corresponding primary aromatic amine from the crude reaction product, and distilling the organic phase in a distillation column, wherein the corresponding primary aromatic amine is removed via a side offtake in a stripping section of the column, low boilers and water are removed at the top of the column, and high boilers are removed at the bottom of the column.

18. The process according to claim 17, wherein the distillation column comprises a dividing wall column.

19. The process according to claim 1, wherein the reaction is carried out in a single-stream plant comprising two or more tube reactors connected in series, wherein a reaction temperature in a first tube reactor of the two or more tube reactors is 200 to 220° C., and wherein a reaction temperature in a second tube reactor of the two or more tube reactors is 230 to 270° C.

* * * * *